United States Patent [19]

Turner et al.

[11] Patent Number: 4,662,887
[45] Date of Patent: May 5, 1987

[54] PROSTHETIC DEVICES

[75] Inventors: Roger M. Turner, Castleton; Martin S. Swerdlow, North London; Bernard Bate, Chester, all of England

[73] Assignee: Imperial Chemical Industries, Hertfordshire, England

[21] Appl. No.: 745,136

[22] Filed: Jun. 17, 1985

[30] Foreign Application Priority Data

Jun. 15, 1984 [GB] United Kingdom ............... 8415265

[51] Int. Cl.⁴ .............................................. A61F 2/02
[52] U.S. Cl. .................................................... 623/16
[58] Field of Search ........................... 623/16; 128/924

[56] References Cited

U.S. PATENT DOCUMENTS

| | | | |
|---|---|---|---|
| 4,181,983 | 1/1980 | Kulkarni | 623/16 |
| 4,206,516 | 6/1980 | Pilliar | 623/16 |
| 4,227,265 | 10/1980 | Frey | 623/16 |
| 4,281,420 | 8/1981 | Raab | 623/16 |

Primary Examiner—Gregory E. McNeill
Attorney, Agent, or Firm—Cushman, Darby & Cushman

[57] ABSTRACT

A high modulus endoprosthetic device comprising a polyaryletherketone and optionally reinforcement which may be fibrous, particulate or relatively massive. Loss of reinforcement to the body tissues may be reduced by provision of polymer rich layer at the surface of the device, particularly in locations where reinforcement is exposed at the surface or is likely to be exposed due to tissue or other abrasion.

12 Claims, 6 Drawing Figures

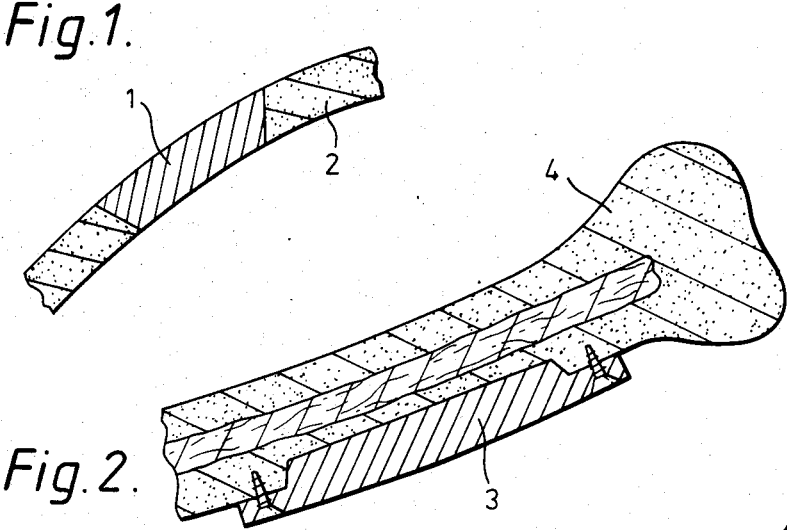
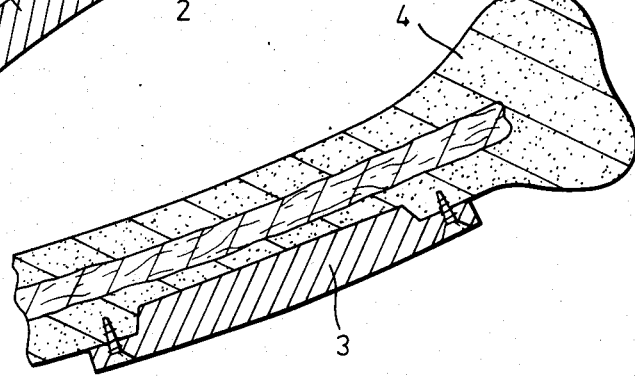
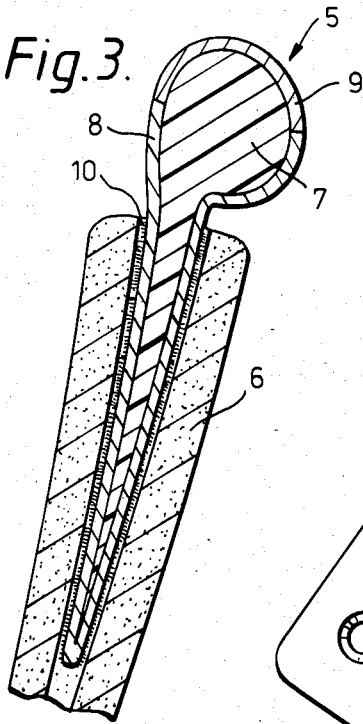
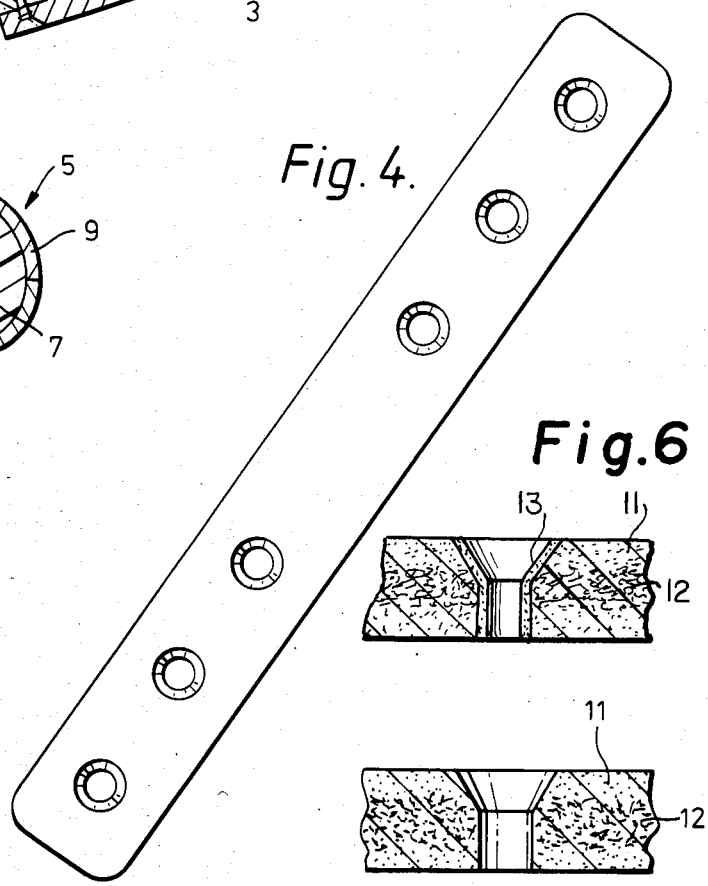
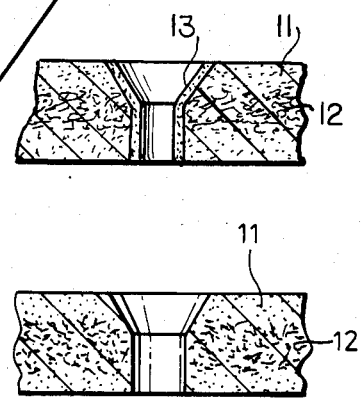

PROSTHETIC DEVICES

This invention relates to shaped products adapted for location and use within the living body.

Endoprosthetic and other devices of many shapes, configurations and properties are commonly employed within the living body. The present invention relates to those of such devices which have or comprise a component having a strength and stiffness comparable with that of the bony tissues of the body, and includes devices which comprise also a softer or more flexible and/or harder or less flexible component. For convenience such devices may be referred to hereinafter was "high-modulus devices").

Many such devices will be known to the skilled practitioner. Examples of such devices are so-called "bone plates" which are used to hold fractured bones in alignment during healing; plates or inserts used to cover damage to a bone or to replace damaged or destroyed bone, or to reinforce it, for example in the skull or long bones; and components of replacement joints, particularly the hip joint, although the invention is not limited to such devices. High modulus devices must be of a shape, configuration and properties appropriate to their proposed application, being preferably such that they are acceptable to the living tissue with which they are likely to come into contact when in use for a time sufficient for them to perform their intended function without unacceptable damage or undue discomfort to the individual in whose body the device is located, and ideally for a period such that if appropriate they need not be removed from the body during the life of the individual.

A wide range of materials have been suggested for use in the manufacture of high modulus devices, ranging from metals, such as stainless steel and titanium, through ceramics and plastics to composite materials comprising for example a fibre-filled polymer material, for example carbon-fibre-filled epoxy resin. All such materials have been found to have disadvantages. Thus metal devices of adequate strength may have too high a modulus so that when used for example in bone plates the healing of the bone is impaired. Fibre-resin composites sometimes initiate a tissue reaction which may be a response to the chemical nature of the device or which may in some cases result from the presence in the tissue adjacent the device of fine particles of the fibrous component of the device, resulting possibly from erosion of the fibre where it reaches the surface of the device.

According to one aspect the present invention provides a high modulus device of shape, configuration and chemical properties appropriate to its proposed location and use within the living body, said high modulus device comprising a polyaryletherketone.

The polyaryletherketone component of the polymer composition may be a polymer which contains the repeat units

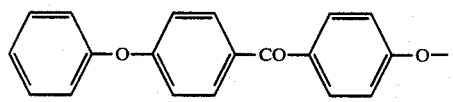

or the repeat units

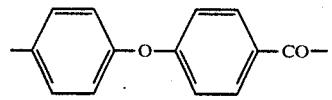

alone or in conjunction with each other and/or in conjunction with other units which may be repeat units.

Other units which may be present in the polyaryletheketone are typically of the general formula

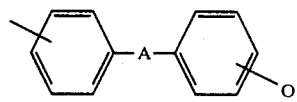

where
A is a direct link, a sulphur atom, a divalent hydrocarbon radical or a group $-Q-(Ar-Q^1)_n$ in which
Q is $-CO-$, $-SO-$ or $-O-$;
Q is $-CO-$, $-SO-$ or $-O-$;
Ar is a divalent aromatic radical; and
n is 0, 1, 2 or 3.

In the formula III, if the group A is a divalent hydrocarbon radical it is typically though not essentially a phenylene group or a dimethylmethylene group $(-C(CH_3)_2)$. The aromatic radical Ar is preferably a divalent aromatic radical selected from phenylene, biphenylylene or terphenylylene.

We prefer that the polyaryletherketone is a crystalline polymer containing the repeat units I. Especially preferred are such polymers which are tough and have an inherent viscosity (IV) of at least 0.7, as is described in more detail in our European patent publication No. 001 879. Inherent viscosity is measured at 25° C. on a solution of the polymer in concentrated sulphuric acid of density 1.84 g cm$^{-3}$, said solution containing 0.1 g of polymer per 100 cm$^3$ of solution. As an alternative to IV, an indication of the average molecular weight of the polymer may be obtained by measuring the melt viscosity of the polymer. Preferred polymers have a melt viscosity of at least 0.1 KNs/m$^2$, which corresponds to an IV of 0.7. The melt viscosity is measured using a ram extruder fitted with a 3.175×0.5 mm die and operating at 400° C. and a sheer rate of 1000s$^{-1}$. Our European Pat. No. 102 159 also includes information relating to polymeric and filler components that are suitable for use in the present invention.

For convenience hereinafter the polyaryletherketone will be referred to as PEEK.

While we have found PEEK to be particularly well tolerated by living tissues, final determination of suitability for use in any particular location may be determined by use of a sample test as described subsequently, and while it may merely form a component of the high modulus device of the invention preferably PEEK will form the greater part of and more preferably the entire surface of the high modulus device which in use will come into contact with living tissue.

The polymer component of the high modulus device may consist of PEEK alone or may comprise a plurality of polymers, which may be in uniform admixture or otherwise, the presence of any polymeric component additional to the PEEK, and its distribution, being determined with the requirements of the high modulus device, for example its tissue acceptability, and the need for compatibility of the components one with another and their handling and processing characteristics, in mind.

For example, certain advantageous properties may be obtained by the use in certain high modulus devices of a composite polymer comprising PEEK and a fluorine-containing polymer, for example PTFE, which may be distributed for example in the form of particles in a matrix of PEEK or may form a coating to at least part of the surface of the device. Polyethersulphone polymers also may be used in admixture with PEEK. The PEEK in such compositions will usually form from 15 to 99.5% by weight, conveniently from 30 to 99.5% by weight, and more conveniently from 50 to 99.% by weight. Many other polymers, including, for example, high density polyethylene may also be included as a polymeric component with the PEEK and optionally other constituents, but the effect of the presence of polymers having different physical and chemical properties, particularly relatively low softening polymers, upon the processing and properties of the composite must be taken into consideration. Also the effect of processing conditions, for example the high temperature needed to soften PEEK (about 380° C.) during shaping, may degrade certain other polymers.

In addition to the use of PEEK as sole component of the device of the invention, or as one of a plurality of polymeric components, the invention comtemplates its use as a component, optionally the matrix, of a composite comprising one or more structural elements which may be for example fibrous, particulate or relatively massive, and which element may be uniformly or non-uniformly distributed in the device, and accordingly, the invention provides a high modulus device which is a composite comprising a polyarylether ketone and a structural component or reinforcement.

Reinforcement of polymers particularly by fibres is well-known and the selection of the size, distribution, proportions and fibre content in fibre-reinforced compositions in order to impart particularly desired properties thereto is well-established technology.

The fibre component of high modulus device may be any of the range of fibre materials that are available and that are compatible with the polymer matrix with which they are to be associated and which are capable of imparting the desired properties. Preferred examples are carbon and glass fibres, although fibres of other materials, for example mineral, eg. aluminosilicate, and organic, eg poly-para-phenylene terephthalamide, are not excluded.

Mixtures of fibres of different composition and/or dimensions may be present in the high modulus product and the fibres may be used in the form of continuous or discontinuous fibres, for example in the form of rovings, chopped and milled fibres, cloths or mats. The distribution of the fibres in the device may be random or orientated to impart particular flexural and other properties suited to the particular use envisaged and the method employed in the production of the device of the invention will be selected in this light. For example, where it is important that, say, relatively long fibres should lie in a particular direction, then a method, for example filament winding, pin winding, extrusion or hand lay up may be appropriate while where random distribution of short fibres is acceptable manufacture by moulding chopped chips or granules containing a fibre/polymer mix may be employed. In production of the shaped device the fact that PEEK is thermoplastic facilitates final shaping, for example in a heated mould.

Reference has been made to the fact that tissue reaction to endoprostheses sometimes occurs and one cause of such reaction may be release into the tissues of fragments of reinforcement of composite endoprostheses. Such release may come about in several ways - including abrasion during affixing of the endoprosthesis, for example by the action of tools or attachment means employed, or abrasion by adjacent living tissues.

We have found it to be advantageous if at least a substantial proportion, and preferably the whole of the surface of the high modulus device of the invention which in use will contact living tissue consists of tissue compatible polymer (particularly PEEK) with little or no exposure to the tissues of any reinforcement, (including filler or inclusions) whether fibrous or otherwise, and this may be attained by employing production methods whereby uneven distribution of reinforcement is attained, giving a high modulus product in which at least the abrasion-vulnerable surface region is substantially free of the reinforcement. Such methods may include hand layup techniques, multiple injection moulding techniques, whereby for example a peripheral region is formed from polymer and an internal, reinforced, region created by subsequent injection, by gel coating techniques, by application of a coating of the polymer upon a core which optionally may be subjected to a further shaping operation, for example by moulding at high temperatures, as appropriate, etc. Obviously, any operation to which the device is subjected subsequent to formation of the reinforcement-free surface should preferably be such that reinforcement is not thereby exposed, at least not in a region which in use will contact living tissue or, if it so exposed, it should preferably be in a region which may subsequently be protected, for example by application of polymer conveniently from solution or melt or other appropriate sealing means.

The thickness of the polymer surface layer will be chosen such that it is effective in reducing reinforcement release. The polymer surface layer may be very thin, of the order of a few microns, or it may be relatively thick, up to several millimeters, depending for example upon the proposed application of the high modulus device, the degree of erosion to which it is likely to be subjected, the amount of flexing (which might for example produce cracking of the polymer and hence exposure of underlying reinforcement), the length of time for which it is anticipated that it might remain in the body, and the dimensions of the device. Preferably it will be between 0.1 and 1 mm thick. The thickness of the surface layer may be different in different regions of the surface.

Particular mention has been made of the use of fibres as co-components with PEEK of the high modulus device of the invention, but it will be understood that the invention in its broadest sense encompasses any device for use as described herein in which the surface, or part of it as appropriate is rendered tissue compatible by the concentration at that surface of any suitable polymer. Thus, it includes devices comprising core components comprising particulate or relatively massive and particularly fibrous (especially carbon and glass fibre) components provided with a surface layer of a tissue compatible polymer. In a further embodiment, for example, there is provided a device comprising a core component at least part of the surface of which comprises a coating or layer of a tissue compatible polymer, said polymer being held to the core by means of adhesion or by a mechanical key effect, as by penetration to an appropriate depth of the core component. Such core components may comprise a tissue compatible polymer, for example a polymer found in the surface layer, or it may comprise other less tissue compatible polymers and non polymeric materials, which may be metallic, polymeric, or ceramic or mixtures of these which themselves may not be tissue compatible. Thus, it may be advantageous for example to employ as or in a core component a composite material as described in one of the specifications of European Pat. Nos. 21682, 55035 or 102159, where the core component may be shaped to a desired form for example by moulding or machining and provided with a complete or partial surface coating or layer of a tissue compatible polymer. Adhesion of the said surface may be by the natural adhesive properties of one or more of the components, by the use of an appropriate adhesive, by mechanical keying of the surface in the core for example by penetration of the surface or adhesive material into pores in the surface of the core or by a combination of any of these. The surface of the core component may, where appropriate, be treated to create a surface character conducive to adhesion to it of the surface material. This may be effected for example by any convenient means, including machining, blowing, drilling, abrading, irradiation, chemical treatment, etc.

Even where high modulus device is provided with a tissue compatible surface layer, preparation of the device for insertion in the body may expose potentially undesirable reinforcement, for example in the course of drilling holes to take fixing screws as in a bone plate, and preferably such preparation will be carried out by a technique which generates a polymer surface over the reinforcement such as by forming the holes or following the drilling of the holes by a process in which the exposed surface is melted or softened so that polymer flows over any exposed reinforcement. Alternatively, a further treatment may be employed whereby the surface may be covered by a further layer of polymer for example by applying a polymer coat either to the entire high modulus device, or locally, in the vicinity of and covering any exposed reinforcement, such as in a further moulding process. The location of inserts in the form of 'linings' for holes drilled in the devices of the invention may be effective also in sealing off potentially harmful reinforcement, the material of such inserts may conveniently be of tissue compatible polymer, or it may be of a suitable metal.

The devices of the invention may be employed in the living body in a wide variety of applications and the physical characteristics of the device, dimensions, chemical nature, modulus etc will be selected in the light of the proposed use.

Thus, we have found that for use as bone plates a composite comprising long fibre carbon fibre (of the order of several millimeters say 5–20 mm) and PEEK is a convenient composition, whereas for devices which in use are to be employed as bone inserts or joint components it may be preferred to mould a massive core component of a ceramic material of suitable strength and modules, and to provide at least part of the core with a surface layer of tissue compatible polymer. For use as an intramedullary rod we prefer to use a long carbon fibre core.

According to a further aspect of the invention there is provided a device adapted for use in the living body where intimate association is desired between the device and living tissue, comprising a high modulus device as hereinbefore described, at least part of the surface thereof being of a fibrous nature the surface fibres being of a material which is tissue compatible and which in the event of erosion do not initiate tissue reaction. Such fibrous material will preferably be separated from any reinforcement by a layer of tissue compatible material as hereinbefore described.

The specification of Canadian Pat. No. 1,141,293 describes one method of preparing fibres of dimensions particularly appropriate to the encouragement of living cell ingrowth, and fibres employed in this aspect of the present invention are preferably of dimensions and compositions as described therein. The surface fibrous component may be formed in situ, for example by drawing part or all of material of the surface area of the device into fibres of the desired dimensions and configuration, or by causing fibres, either in the form of a mat or individually to adhere to the surface of the device as they are spun, for example by using the device as a mandrel, etc.

It is conventional to shape certain endoprostheses to conform to a desired form, for example curvature of a bone, and it has been suggested to use electrically conducting reinforcement components, particularly carbon fibre, as heating elements, by leaving carbon fibres projecting from the surface of such devices to which a source of electricity may be attached. Obviously such exposed fibres are undesirable for the reasons given above.

The present invention further provides a shapable high modulus device comprising a thermoformable polymeric component and a reinforcement which is electrically conducting, but which is not exposed at the surface of the device. Shaping may be effected by heating the device by induction of a current within the reinforcement to a temperature such that the high modulus device is shapable, shaping the device and allowing it to cool to a temperature at which it retains its improved shape. Carbon fibres are particularly effective as reinforcement, preferably continuous fibres and disposed in accordance with known induction heating technology.

The use of PEEK as the matrix of a fibrous or particulate filler is particularly advantageous in that it is thermoformable to a desired contour, and may be drilled for example by thermal lance as well as by more conventional means.

The invention is illustrated by the following Examples, which describes the preparation and testing for tissue compatibility of a PEEK carbon fibre high modulus device, but it will be understood, however, that by selection of other appropriate components and preparative techniques other devices may conveniently be made.

Illustrated in sectional view in the drawings are, in FIG. 1, a cranial plate 1 in situ within an aperture cut into the skull 2; in FIG. 2 an insert 3 in a long bone 4 from which part of the bone had been removed; and in FIG. 3 a femur head replacement 5 in situ within a femur 6. This last device comprises a core component 7 of a cement composition as described in European Patent Specification No. 21682 and comprising a surface coating of PEEK 8, a bearing surface 9 of titanium and a fibrous surface layer 10.

A bone plate shown in perspective in FIG. 4 is shown also in enlarged section in FIG. 5, to illustrate the use of a PEEK outer coating 11 upon a core region comprising a PEEK-carbon fibre composite 12. FIG. 6 shows the presence of PEEK 13 also after refilling of the screw holes and redrilling.

EXAMPLE 1

A sample of "Victrex" PEEK Grade 45 G (ex I.C.I) was injection moulded using an Arburg injection moulding machine with plasticising screw and barrel temperature 380° C. into a heated mould held at 150° C. to give discs 5 mm diameter and 1 mm thick. These had a flexural modulus of 3.8 GN/m² and flexural strength 156 MN/m².

EXAMPLE 2

A sample of "Victrex" PEEK 450 CA 30 chips (ex I.C.I) comprising 45 G PEEK and 30% w/w short carbon fibre (less than 1 mm length) in intimate admixture was injection moulded generally as described in Example 1 except that they were moulded to form bars. The bars so obtained had flexural modulus 21 GN/m² and flexural strength 343 MN/m².

EXAMPLE 3

A Granulated PEEK composite comprising 50% carbon fibre of average fibre length 10 mm was injection moulded at 380° C. to form a composite sheet having flexural modulus 41 GN/m and flexural strength 372 MN/m².

EXAMPLE 4

A quasi isotropic sheet comprising 16 plies of long carbon fibre of average length 25 mm preimpregnated with PEEK 45 G, was compression moulded at 400° C. to give a sheet product of dimensions 200×150×3 mm having a flexural modulus of 47 GN/m². The sheet so obtained was shaped to give a curvature of 15 mm radius at 400° C. and under 6 tons pressure to give a product from which bars 5 cm×1 cm were cut to provide a bone plate of form suitable for attachment to the femur of a cat. Holes were drilled to take attachment screws, and the plate attached to the femur of a cat. After 3 months minor tissue reactions were visible, which was shown microscopically to be related probably to particles of carbon fibre which were concentrated predominantly in the vicinity of the holes.

Samples of all the above materials were placed intramuscularly with the legs of dogs and allowed to remain undisturbed for 30 weeks. At the end of that time the samples from Examples 1 and 2 showed benign response, those from Examples 3 and 4 showed slightly more response but considerably less than samples made from carbon fibre epoxy resin.

EXAMPLE 5

Example 4 was repeated except that subsequent to drilling the holes the plate was reintroduced into a mould cavity larger by 1 mm in all dimensions that that used in preparing the original bar. The bar was further moulded with a sufficient of the same PEEK resin to coat it to a depth of 1 mm and to fill the screw holes, which subsequently were drilled out again without exposing the fibre reinforcement.

Attachment was to a living bone as described in Example 4, and after 3 months no tissue reaction was evident.

We claim:
1. A high modulus prosthetic device comprising a polyaryletherketone, wherein said polyaryletherketone is a crystalline polymer of inherent viscosity of at least 0.7.
2. A high modulus prosthetic device according to claim 1 comprising a polymeric component containing repeat units of

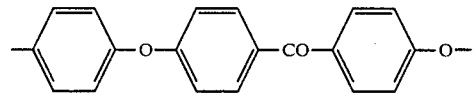

and/or of

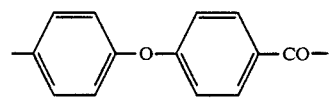

3. A high modulus prosthetic device according to claim 1 comprising units of

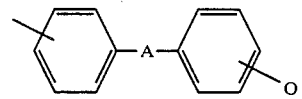

where A is a direct link, a sulphur atom, a divalent hydrocarbon radical or a group —Q—(Ar—Q¹)$_n$ in which Q is —CO—, —SO—, or —O—, Ar is a divalent aromatic radical; and n is 0, 1, 2 or 3.
4. A high modulus prosthetic device according to claim 1 further comprising fibrous or particulate reinforcement.
5. A high modulus prosthetic device according to claim 4, in which the reinforcement is of carbon fibre.
6. A high modulus prosthetic device comprising a reinforcing material and a tissue compatible polymer, said tissue compatible polymer disposed such that no reinforcing material is exposed to tissue within the body.
7. A high modulus prosthetic device according to claim 6 in which the polymeric component is present in the form of a layer at the surface of said device.
8. A high modulus prosthetic device according to claim 1 which further comprises a relatively massive reinforcing core component.
9. A high modulus prosthetic device according to claim 3, wherein A is selected from the group consisting of a phenylene group and a dimethylmethyline group.
10. A high modulus prosthetic device according to claim 3, wherein Ar is selected from the group consisting of phenylene, biphenylene or terphenylylene.
11. A method of preparing a high modulus polyaryletherketone endoprosthetic device comprising the steps of:
(a) forming said device from the polymer of claim 1 in a desired shape by compression or injection molding;
(b) drilling holes in said device to allow screw attachment of said device within the body; and
(c) coating said drilled device with a further layer of said polyaryletherketone.
12. Method of using the high modulus prosthetic device of claim 1 which comprises locating and affixing said device within the body.

* * * * *